United States Patent
Inayama et al.

(10) Patent No.: US 8,664,430 B2
(45) Date of Patent: Mar. 4, 2014

(54) PENTAERYTHRITOL TETRAESTER

(75) Inventors: Toshihiro Inayama, Mie (JP); Satoshi Hiyoshi, Mie (JP); Nobuhito Amemiya, Mie (JP); Shigehisa Kishimoto, Mie (JP)

(73) Assignee: KH Neochem Co., Ltd., Tokyo (JP)

( * ) Notice: Subject to any disclaimer, the term of this patent is extended or adjusted under 35 U.S.C. 154(b) by 0 days.

(21) Appl. No.: 13/813,688

(22) PCT Filed: Jun. 30, 2011

(86) PCT No.: PCT/JP2011/065107
§ 371 (c)(1),
(2), (4) Date: Feb. 1, 2013

(87) PCT Pub. No.: WO2012/026212
PCT Pub. Date: Mar. 1, 2012

(65) Prior Publication Data
US 2013/0131373 A1 May 23, 2013

(30) Foreign Application Priority Data
Aug. 24, 2010 (JP) .................................. 2010-187571

(51) Int. Cl.
*C07C 69/025* (2006.01)

(52) U.S. Cl.
USPC ........................................................ 560/129

(58) Field of Classification Search
USPC ........................................................ 560/129
See application file for complete search history.

(56) References Cited

U.S. PATENT DOCUMENTS 5,395,544 A   3/1995   Hagihara et al.
6,228,820 B1  5/2001   Sakai et al.

FOREIGN PATENT DOCUMENTS

| CN | 1202880 A | 12/1998 |
| JP | 6-17073 A | 1/1994 |
| JP | 6-25682 A | 2/1994 |
| JP | 2002-129177 A | 5/2002 |
| WO | 97-11933 A1 | 4/1997 |
| WO | 2012/026303 A1 | 3/2012 |

OTHER PUBLICATIONS

U.S. Appl. No. 13/813,718 to Toshihiro Inayama et al., which was filed Feb. 1, 2013.
Yasughiro Kawaguchi, "Recent Movement for Refrigerating Machine oil.", Lubricant Economy, Jun. 2004, pp. 17-21.
U.S. Appl. No. 13/813,695 to Toshihiro Inayama et al., which was filed Feb. 1, 2013.
Search report from International Application No. PCT/2011/065107, mail date is Aug. 9, 2011.
International Preliminary Report on Patentability No. PCT/JP2011/065107, mail date is Sep. 8, 2011.
Taiwan Office action, mail date is Apr. 8, 2013.

*Primary Examiner* — Yevgeny Valenrod
*Assistant Examiner* — Karen Cheng
(74) *Attorney, Agent, or Firm* — Greenblum & Bernstein, P.L.C.

(57) ABSTRACT

A pentaerythritol tetraester which is a mixed ester of pentaerythritol and carboxylic acids is provided, wherein the carboxylic acids comprise isobutyric acid and 2-ethylhexanoic acid and the molar ratio of isobutyric acid to 2-ethylhexanoic acid in the carboxylic acids is 36/64 to 83/17. The pentaerythritol tetraester may be used in a refrigerant oil or the like which exhibits excellent miscibility with a difluoromethane refrigerant among other properties.

2 Claims, No Drawings

PENTAERYTHRITOL TETRAESTER

RELATED-ART DOCUMENTS

Patent Document
  Patent Document 1: JP 2002-129177 A
Non-Patent Document
  Non-Patent Document 1: Junkatsu Keizai, June 2004 (No. 460), p. 17

TECHNICAL FIELD

The invention relates to a pentaerythritol tetraester that may be used in an industrial lubricant (e.g., refrigerant oil) or the like.

BACKGROUND ART

In recent years, hydrofluorocarbons (HFC) that have zero ozone depletion potential (ODP) as well as a relatively low global warming potential (GWP) have been used as refrigerants for refrigerators. A difluoromethane refrigerant (HFC-32) has a low GWP that is about 1/3rd to 1/4th of that of other refrigerants currently used (e.g., R-410A which is a mixture of difluoromethane and pentafluoroethane and R-407C which is a mixture of difluoromethane, pentafluoroethane and 1,1,1,2-tetrafluoroethane). Moreover, the difluoromethane refrigerant also has a coefficient of performance (COP) higher than that of R-410A, R-407C and the like by about 5 to 13% and therefore is a preferable refrigerant from the viewpoint of energy-saving (see Non-Patent Document 1).

Patent Document 1 discloses an ester of pentaerythritol and a fatty acid that is used in a refrigerant oil for the difluoromethane refrigerant. However, the ester disclosed in Patent Document 1 is not satisfactory in that it does not exhibit sufficient miscibility with the difluoromethane refrigerant, for example.

SUMMARY OF THE INVENTION

Technical Problem

An object of the present invention is to provide a pentaerythritol tetraester that may be used in a refrigerant oil or the like that exhibits excellent miscibility with a difluoromethane refrigerant among other properties.

Solution to Problem

The invention provides the following pentaerythritol tetraester.

[1] A pentaerythritol tetraester that is a mixed ester of pentaerythritol and carboxylic acids, the carboxylic acids comprising isobutyric acid and 2-ethylhexanoic acid wherein a molar ratio of isobutyric acid to 2-ethylhexanoic acid (i.e., isobutyric acid/2-ethylhexanoic acid ratio) is 36/64 to 83/17.

[2] The pentaerythritol tetraester according to [1], wherein the carboxylic acids consist of isobutyric acid and 2-ethylhexanoic acid.

Advantageous Effects of the Invention

The invention thus provides a pentaerythritol tetraester that may be used in a refrigerant oil or the like exhibiting excellent miscibility with a difluoromethane refrigerant among other properties.

DESCRIPTION OF EMBODIMENTS

Preferred embodiments of the invention are described in detail below.

A pentaerythritol tetraester according to the invention is a mixed ester of pentaerythritol and carboxylic acids, the carboxylic acids comprising isobutyric acid and 2-ethylhexanoic acid wherein the molar ratio of isobutyric acid to 2-ethylhexanoic acid (i.e., isobutyric acid/2-ethylhexanoic acid ratio) is 36/64 to 83/17. However, the pentaerythritol tetraester may achieve the effects of the invention even if said molar ratio does not fall within the above range. Such a pentaerythritol tetraester is also included within the scope of the invention. The term "pentaerythritol tetraester" used herein refers to a compound obtained by completely esterifying the four hydroxyl groups of pentaerythritol with four carboxylic acid molecules.

The term "mixed ester" used herein includes (i) a pentaerythritol tetraester in which the constituent carboxylic acids in one molecule comprise both isobutyric acid and 2-ethylhexanoic acid; (ii) a mixture of an ester of pentaerythritol and carboxylic acids comprising isobutyric acid, and an ester of pentaerythritol and carboxylic acids comprising 2-ethylhexanoic acid; and (iii) a mixture of (i) and (ii).

The pentaerythritol tetraester according to the invention may comprise a pentaerythritol triester and the like as impurities.

The carboxylic acids which constitute the mixed ester may comprise other carboxylic acids in addition to isobutyric acid and 2-ethylhexanoic acid. Examples of the other carboxylic acids include linear aliphatic carboxylic acids (e.g., acetic acid, propionic acid, butyric acid, pentanoic acid, hexanoic acid, heptanoic acid, octanoic acid, nonanoic acid, decanoic acid, dodecanoic acid, tetradecanoic acid, hexadecanoic acid, and octadecanoic acid), branched aliphatic carboxylic acids (e.g., 2-methylbutyric acid, 3-methylbutyric acid, 2,2-dimethylpropanoic acid, 2-ethylbutyric acid, 2-methylpentanoic acid, 4-methylpentanoic acid, 2-methylhexanoic acid, 2-ethylpentanoic acid, 2-ethyl-2-methylbutyric acid, 2,2-dimethylpentanoic acid, 2-methylheptanoic acid, 3-ethylhexanoic acid, 2-ethyl-2-methylpentanoic acid, 3,5,5-trimethylhexanoic acid, 2-methyloctanoic acid, 2,2-dimethylheptanoic acid, isotridecanoic acid, and isostearic acid), and the like. The content of the other carboxylic acids in the carboxylic acids comprising isobutyric acid and 2-ethylhexanoic acid may be in a range without impairing excellent properties (e.g., miscibility with a difluoromethane refrigerant) of the pentaerythritol tetraester. A molar ratio of the other carboxylic acids to the sum of isobutyric acid and 2-ethylhexanoic acid (i.e., the other carboxylic acids/the sum of isobutyric acid and 2-ethylhexanoic acid ratio) is preferably 0/100 to 5/100.

In the present invention, the carboxylic acids which constitute the mixed ester preferably consist of isobutyric acid and 2-ethylhexanoic acid.

The pentaerythritol tetraester according to the invention may be produced, for example, by reacting pentaerythritol, isobutyric acid, 2-ethylhexanoic acid and optionally the other carboxylic acids at 120 to 250° C. for 5 to 60 hours, in the presence of a catalyst.

Examples of the catalyst include mineral acids, organic acids, Lewis acids, organometals, solid acids, and the like. Specific examples of the mineral acids include hydrochloric acid, hydrofluoric acid, sulfuric acid, phosphoric acid, nitric acid, and the like. Specific examples of the organic acids include p-toluenesulfonic acid, benzenesulfonic acid, butanesulfonic acid, propanesulfonic acid, ethanesulfonic acid, methanesulfonic acid, and the like. Specific examples of the Lewis acids include boron trifluoride, aluminum chloride, tin tetrachloride, titanium tetrachloride, and the like. Specific examples of the organometals include tetrapropoxytitanium, tetrabutoxytitanium, tetrakis(2-ethylhexyloxy)titanium, and the like. Specific examples of the solid acids include a cation-exchange resin and the like.

The sum of the amount (mol) of isobutyric acid, the amount (mol) of 2-ethylhexanoic acid and the amount (mol) of the other carboxylic acids is preferably larger than the amount (mol) of the hydroxyl groups of pentaerythritol by a factor of 1.1 to 1.4.

In the reaction of pentaerythritol, isobutyric acid, 2-ethylhexanoic acid and optionally the other carboxylic acids, a solvent may be used, examples of which include benzene, toluene, and xylene.

It is preferable to carry out the reaction of pentaerythritol, isobutyric acid, 2-ethylhexanoic acid and optionally the other carboxylic acid while removing from the reaction mixture the water produced during the reaction. It should be noted that isobutyric acid may be incidentally removed from the reaction mixture when the water produced during the reaction is being removed.

After completion of the reaction, the resulting pentaerythritol tetraester may optionally be purified by a method normally used in synthetic organic chemistry (e.g., washing with water and/or an alkaline aqueous solution, a treatment with activated carbon, an adsorbent, or the like, and various types of chromatography methods and distillation methods).

The pentaerythritol tetraester according to the invention exhibits excellent miscibility with a difluoromethane refrigerant, excellent low-temperature fluidity, and excellent lubricity, among other properties.

When the pentaerythritol tetraester according to the invention is used in a refrigerant oil for an air conditioner, the kinematic viscosity of the pentaerythritol tetraester at 40° C. is preferably 20 to 40 mm$^2$/sec. The pentaerythritol tetraester preferably has a two-phase separation temperature of −15° C. or lower.

The pentaerythritol tetraester according to the invention may be used in a refrigerant oil, as well as in an engine oil, a gear oil, grease, a plasticizer, and the like.

The refrigerant oil using the pentaerythritol tetraester according to the invention may be a refrigerant oil comprising the pentaerythritol tetraester of the invention and a lubricant additive, for example. In the refrigerant oil using the pentaerythritol tetraester according to the invention, the pentaerythritol tetraester is used as a lubricant base oil.

Examples of the lubricant additive include an antioxidant, a wear-reducing agent (e.g., anti-wear agent, anti-seize agent, and extreme pressure agent), a friction modifier, an acid scavenger, a metal deactivator, an anti-foaming agent, and the like which are usually used as lubricant additives. The amount of each additive in the refrigerant oil is preferably 0.001 to 5 wt %.

The pentaerythritol tetraester according to the invention may be used in combination with other lubricant base oils. Examples of such additional lubricant base oils include a mineral oil, a synthetic base oil, and the like.

Examples of the mineral oil include paraffinic crude oils, intermediate base crude oils, naphthenic crude oils, and the like. A refined oil obtained by purifying any of said mineral oils via distillation or the like may also be used.

Examples of the synthetic base oil include poly-α-olefins (e.g., polybutene, polypropylene, and α-olefin oligomers having 8 to 14 carbon atoms), aliphatic esters other than the pentaerythritol tetraester of the invention (e.g., fatty acid monoesters, fatty acid esters of a polyhydric alcohol, and aliphatic polybasic acid esters), aromatic esters (e.g., aromatic monoesters, aromatic esters of a polyhydric alcohol, and aromatic polybasic acid esters), polyalkylene glycols, polyvinyl ethers, polyphenyl ethers, alkylbenzenes, carbonates, synthetic naphthene, and the like.

The pentaerythritol tetraester according to the invention has an excellent ability to dissolve lubricant additives such as a metal deactivator (e.g., benzotriazole) and a silicon-based anti-foaming agent. The lubricant additive is dissolved in the lubricant in order to prolong the lifetime of the lubricant and the system containing the lubricant, for example. The lubricant additives generally have low solubility in a pentaerythritol ester (see JP H10-259394 A). Moreover, benzotriazole has low solubility in a mineral oil and/or a synthetic oil (see JP S59-189195 A). However, benzotriazole was found to be highly soluble in any of the pentaerythritol tetraesters according to the invention. For example, solubility of Tetraester 1 (see Example 1), which belongs to the pentaerythritol tetraesters according to the invention, was at least 0.007 g/g at 25° C. and showed excellent solubility of benzotriazole. The pentaerythritol tetraester according to the invention containing dissolved benzotriazole exhibits excellent low-temperature fluidity and excellent anti-wear property.

Moreover, the machines in which the pentaerythritol tetraester according to the invention has been used as a lubricant can be easily cleaned (washed) by using a detergent such as a fluorine-based detergent and an alcohol-based detergent.

EXAMPLES

The invention is further described below by providing Examples, Reference Examples, and Test Examples. However, the invention is not limited to the examples.

The nuclear magnetic resonance spectrum of each of the pentaerythritol tetraesters produced in Examples 1 to 3 and Reference Example 1 was measured, and the molar ratio of isobutyric acid to 2-ethylhexanoic acid was calculated by the formula shown below.

The nuclear magnetic resonance spectrum was measured by using the following instrument and method.

Measurement instrument: GSX-400 (400 MHz) manufactured by JEOL Ltd.

Measurement method: $^1$H-NMR (standard substance: tetramethylsilane; solvent: CDCl$_3$)

Isobutyric acid/2-ethylhexanoic acid=integral value of peak X/integral value of peak Y In the above formula, peak X corresponds to the peak of the hydrogen atom of the methine group of isobutyric acid, and peak Y corresponds to the peak of the hydrogen atom of the methine group of 2-ethylhexanoic acid.

The nuclear magnetic resonance spectrum of the pentaerythritol tetraester produced in Examples 4 was measured, and the molar ratio of isobutyric acid, 2-ethylhexanoic acid and 3,5,5-trimethylhexanoic acid was calculated by the formula shown below.

Isobutyric acid/2-ethylhexanoic acid/3,5,5-trimethylhexanoic acid=integral value of peak X/integral value of peak Y/integral value of peak Z In the above formula, peak X corresponds to the peak of the hydrogen atom of the methine group of isobutyric acid, peak Y corresponds to the peak of the hydrogen atom of the methine group of 2-ethylhexanoic acid, and peak Z corresponds to the peak of the hydrogen atom of the methine group of 3,5,5-trimethylhexanoic acid.

Example 1

Production of pentaerythritol tetraester in which the molar ratio of isobutyric acid to 2-ethylhexanoic acid (i.e., isobutyric acid/2-ethylhexanoic acid ratio) is 36/64 (Tetraester 1)

Kyowaad 500 manufactured by Kyowa Chemical Industry Co., Ltd. was used as an adsorbent.

Shirasagi P manufactured by Japan EnviroChemicals, Ltd. was used as activated carbon.

A reactor equipped with a Dean-Stark trap was charged with 340.4 g (2.57 mol) of pentaerythritol (manufactured by Koei Perstorp, Co., Ltd.), 396.8 g (4.50 mol) of isobutyric acid (manufactured by Tokyo Chemical Industry Co., Ltd.), and 1081.8 g (7.50 mol) of 2-ethylhexanoic acid (manufactured by Kyowa Hakko Chemical Co., Ltd.). The mixture was degassed by nitrogen bubbling at room temperature for 30 minutes with stirring.

The mixture was stirred at 163 to 218° C. for 17 hours while nitrogen bubbling was further continued. After the addition of 0.3 g of tetrabutoxytitanium, the reaction mixture was stirred at 220° C. for 21 hours. After completion of the reaction, the reaction mixture was stirred at 195° C. for 1 hour under a reduced pressure of 1.3 kPa to remove unreacted carboxylic acids from the reaction product by distillation. The reaction product was washed at 80° C. for 1 hour with 500 mL of an alkaline aqueous solution containing sodium hydroxide at 2-fold molar excess relative to the acid number of the reaction product. The reaction product was then washed with 500 mL of water at 70° C. for 1 hour (four times). Next, the reaction product was stirred at 100° C. for 2 hours under a reduced pressure of 0.4 kPa with nitrogen bubbling to dry the reaction product.

After the addition of 52.0 g of the adsorbent (corresponding to 4 wt % of the reaction product) and 26.0 g of activated carbon (corresponding to 2 wt % of the reaction product), the mixture was stirred at 102° C. for 2 hours under a reduced pressure of 0.8 kPa with nitrogen bubbling, and then filtered by using a filter aid, to finally obtain 1159 g of Tetraester 1.

Example 2

Production of pentaerythritol tetraester in which the molar ratio of isobutyric acid to 2-ethylhexanoic acid (i.e., isobutyric acid/2-ethylhexanoic acid ratio) is 62/38 (Tetraester 2)

Tetraester 2 was obtained in the same manner as in Example 1, except that the molar ratio of pentaerythritol, isobutyric acid and 2-ethylhexanoic acid (i.e., pentaerythritol/isobutyric acid/2-ethylhexanoic acid ratio) was changed to 1/2.98/1.82.

Example 3

Production of pentaerythritol tetraester in which the molar ratio of isobutyric acid to 2-ethylhexanoic acid (i.e., isobutyric acid/2-ethylhexanoic acid ratio) is 83/17 (Tetraester 3)

Tetraester 3 was obtained in the same manner as in Example 1, except that the molar ratio of pentaerythritol, isobutyric acid and 2-ethylhexanoic acid (i.e., pentaerythritol/isobutyric acid/2-ethylhexanoic acid ratio) was changed to 1/3.60/1.20.

Example 4

Production of pentaerythritol tetraester in which the molar ratio of isobutyric acid, 2-ethylhexanoic acid, and 3,5,5-trimethylhexanoic acid (i.e., isobutyric acid/2-ethylhexanoic acid/3,5,5-trimethylhexanoic acid ratio) is 39/61/5 (Tetraester 4)

Tetraester 4 was obtained in the same manner as in Example 1, except that isobutyric acid, 2-ethylhexanoic acid and 3,5,5-trimethylhexanoic acid were used instead of isobutyric acid and 2-ethylhexanoic acid, and pentaerythritol, isobutyric acid, 2-ethylhexanoic acid and 3,5,5-trimethylhexanoic acid were used in a molar ratio (i.e., pentaerythritol/isobutyric acid/2-ethylhexanoic acid/3,5,5-trimethylhexanoic acid ratio) of 1/1.78/2.78/0.24.

Reference Example 1

Production of pentaerythritol tetraester in which the molar ratio of isobutyric acid to 2-ethylhexanoic acid (i.e., isobutyric acid/2-ethylhexanoic acid ratio) is 31/69 (Tetraester A)

Tetraester A was obtained in the same manner as in Example 1, except that the molar ratio of pentaerythritol, isobutyric acid and 2-ethylhexanoic acid (i.e., pentaerythritol/isobutyric acid/2-ethylhexanoic acid ratio) was changed to 1/1.20/3.60.

[Test Example 1: Measurement of Pour Point]

Pour points of Tetraesters 1 to 4 and A were measured in accordance with JIS K2269-1987 by using an automatic pour point measurement system "RPP-01CML" (manufactured by Rigo Co., Ltd.). The results are shown in Tables 1 and 2.

[Test Example 2: Measurement of Kinematic Viscosity]

Kinematic viscosity of each of Tetraesters 1 to 4 and A at 40° C. was measured in accordance with JIS K2283:2000 by using a Cannon-Fenske viscometer. The results are shown in Tables 1 and 2.

[Test Example 3: Measurement of Two-Phase Separation Temperature]

The two-phase separation temperatures of Tetraesters 1 to 4 and A were measured in accordance with JIS K2211:2009. Specifically, a pressure-resistant glass tube was charged with 0.4 g of the tetraester (Tetraester 1 to 4 or A) and 3.6 g of a difluoromethane refrigerant, and each of the mixtures was cooled from 30° C. at a rate of 0.5° C./min. The temperature at which the mixture was separated into two phases or became cloudy was defined as the two-phase separation temperature. The results are shown in Tables 1 and 2.

[Test Example 4: Measurement of Solubility of Benzotriazole at 5° C.]

0.15 g of benzotriazole was mixed with 4.85 g of the tetraester (Tetraester 1 to 4 or A), and each of the mixtures was heated at 60° C. to obtain a 3 wt % tetraester solution of benzotriazole. After allowing each of the tetraester solutions to stand at 5° C. for 40 hours, the presence or absence of precipitation was verified by visual inspection.

When no precipitation was observed, the solubility of benzotriazole (i.e., the amount (g) of benzotriazole dissolvable in 1 g of the tetraester) at 5° C. was determined to be 0.030 g/g or higher.

When precipitation was observed, the precipitate was removed by filtration (filter paper: No. 5A, manufactured by Kiriyama Glass Works Co), and the filtrate was then subjected to high-performance liquid chromatography (1200 SERIES manufactured by AGILENT; column: YMC Pack Ph A-414, 6.0 (diameter)×300 mm; mobile phase: tetrahydrofuran/0.1% phosphoric acid aqueous solution (in the ratio of 7/3); column temperature: 40° C.; flow rate: 0.7 ml/min; detection: UV (220 nm); sample concentration: 50 g/l; injection volume: 5 μl), and the solubility of benzotriazole (i.e., the amount (g) of benzotriazole dissolvable in 1 g of the tetraester) at 5° C. was determined by an absolute calibration method. The results are shown in Tables 3 and 4.

[Test Example 5: Measurement of Wear Scar Diameter Using the Tetraester Solutions]

0.4 g of benzotriazole was mixed with 19.6 g of the tetraester (Tetraester 1 to 4 or A), and each of the mixtures was heated at 60° C. to obtain a 2 wt % tetraester solution of benzotriazole.

Each of the 2 wt % tetraester solutions was subjected to a wear test by using a Shell four-ball wear tester (manufactured by Shinko Engineering Co., Ltd.) (load: 200 N; rotating speed: 1200 rpm; duration: 30 minutes; temperature: 75° C.; test piece: test ball SUJ-2) to measure the wear scar diameter. The average value of the wear scar diameters on the three stationary balls in both vertical and horizontal directions was taken as the wear scar diameter. The results are shown in Tables 3 and 4. In Tables 3 and 4, a smaller wear scar diameter indicates better anti-wear property of the tetraester solution.

[Test Example 6: Measurement of Pour Point of the Tetraester Solutions]

1.8 g of benzotriazole was mixed with 43.2 g of the tetraester (Tetraester 1 to 4 or A), and each of the mixtures was heated at 60° C. to obtain a 4 wt % tetraester solution of benzotriazole.

The pour points of the 4 wt % tetraester solutions were measured in accordance with JIS K2269-1987 by using an automatic pour point measurement system "RPP-01 CML" (manufactured by Rigo Co., Ltd.). The results are shown in Tables 3 and 4.

In Tables 3 and 4, BZT indicates benzotriazole.

TABLE 1

| Tetraester | Isobutyric acid/ 2-ethylhexanoic acid ratio (molar ratio) | Kinematic viscosity (mm$^2$/sec) | Pour point (° C.) | Two-phase separation temp. (° C.) |
|---|---|---|---|---|
| A (Ref. Example 1) | 31/69 | 37.9 | −57.5 | −4 |
| 1 (Example 1) | 36/64 | 35.2 | −55.0 | −17 |
| 2 (Example 2) | 62/38 | 28.5 | −55.0 | −40 |
| 3 (Example 3) | 83/17 | 23.7 | −52.5 | ≤−50 |

TABLE 2

| Tetraester | Isobutyric acid/2-ethylhexanoic acid/ 3,5,5-trimethylhexanoic acid ratio (molar ratio) | Kinematic viscosity (mm$^2$/sec) | Pour point (° C.) | Two-phase separation temp. (° C.) |
|---|---|---|---|---|
| 4 (Example 4) | 39/61/5 | 36.2 | −50.0 | −18 |

TABLE 3

| Tetraester | Isobutyric acid/ 2-ethylhexanoic acid ratio (molar ratio) | Solubility of BZT at 5° C. (g/g) | Wear scar diameter (mm) 2 wt % tetraester solution of BZT | Pour point (° C.) 4 wt % tetraester solution of BZT |
|---|---|---|---|---|
| A (Ref. Example 1) | 31/69 | 0.018 | 0.58 | −20.0 |
| 1 (Example 1) | 36/64 | 0.028 | 0.49 | −52.5 |
| 2 (Example 2) | 62/38 | ≥0.030 | 0.50 | −52.5 |
| 3 (Example 3) | 83/17 | ≥0.030 | 0.49 | −50.0 |

TABLE 4

| Tetraester | Isobutyric acid/ 2-ethylhexanoic acid/ 3,5,5-trimethylhexanoic acid ratio (molar ratio) | Solubility of BZT at 5° C. (g/g) | Wear scar diameter (mm) 2 wt % tetraester solution of BZT | Pour point (° C.) 4 wt % tetraester solution of BZT |
|---|---|---|---|---|
| 4 (Example 4) | 39/61/5 | ≥0.030 | 0.47 | −50.0 |

As shown in Tables 1 and 2, Tetraesters 1 to 4 had a kinematic viscosity at 40° C. of 23.7 to 36.2 mm$^2$/sec and a pour point of −50.0° C. or lower, indicating excellent low-temperature fluidity. Moreover, Tetraesters 1 to 4 had a two-phase separation temperature of −17° C. or lower, indicating excellent miscibility with the difluoromethane refrigerant.

As shown in Tables 3 and 4, Tetraesters 1 to 4 were highly capable of dissolving benzotriazole, the solubility of which being 0.028 g/g or higher at 5° C. The 4 wt % solutions of benzotriazole in Tetraesters 1 to 4 had a pour point of −50.0° C. or lower, and the wear scar diameters measured with the 2 wt % solutions of benzotriazole in Tetraesters 1 to 4 were 0.50 mm or less. It was thus confirmed that Tetraesters 1 to 4 exhibited excellent low-temperature fluidity and excellent anti-wear properties in the presence of benzotriazole dissolved therein.

INDUSTRIAL APPLICABILITY

The present invention thus provides a pentaerythritol tetraester that may be used in a refrigerant oil or the like which exhibits excellent miscibility with a difluoromethane refrigerant among other properties.

The invention claimed is:

1. A pentaerythritol tetraester that is a mixed ester of pentaerythritol and carboxylic acids, the carboxylic acids comprising isobutyric acid and 2-ethylhexanoic acid wherein a molar ratio of isobutyric acid to 2-ethylhexanoic acid (isobutyric acid/2-ethylhexanoic acid ratio) is 36/64 to 83/17.

2. The pentaerythritol tetraester according to claim 1, wherein the carboxylic acids consist of isobutyric acid and 2-ethylhexanoic acid.

* * * * *